United States Patent [19]

Spalten

[11] Patent Number: 4,558,701
[45] Date of Patent: Dec. 17, 1985

[54] OSTEOBLASTIC STIMULATION IMPLANT

[76] Inventor: Robert Spalten, 9 E. 67th St., New York, N.Y. 10021

[21] Appl. No.: 524,822

[22] Filed: Aug. 19, 1983

[51] Int. Cl.⁴ .............................................. A61N 1/36
[52] U.S. Cl. .................................. 128/419 F; 128/787
[58] Field of Search ............... 128/419 F, 419 R, 777, 128/782, 784, 787

[56] References Cited

U.S. PATENT DOCUMENTS

| | | | |
|---|---|---|---|
| 2,069,112 | 1/1937 | Oppenheim | 128/787 |
| 3,297,021 | 1/1967 | Davis et al. | 128/777 |
| 4,052,754 | 10/1977 | Homsy | 128/419 F |
| 4,175,565 | 11/1979 | Chiarenza et al. | 128/787 |
| 4,214,322 | 7/1980 | Kraus | 128/419 F |
| 4,390,028 | 6/1983 | Okano et al. | 128/777 |

Primary Examiner—William E. Kamm
Attorney, Agent, or Firm—Harry E. Rubens

[57] ABSTRACT

An osteoblastic stimulated implant contacting bone in the body in which is provided a self contained unit positioned between the base of the implant and a cap member, a chamber positioned between the cap member and the base, containing a current generating unit, which can be a piezo electric element, a battery, a coil and magnet, or the like, wherein the movement of the cap towards the base will cause a flow of current into the base member.

2 Claims, 2 Drawing Figures

OSTEOBLASTIC STIMULATION IMPLANT

This invention relates to electrically generated osteoblastic stimulation, and more particularly to a self contained electric stimulator.

Electric currents have been hitherto used to increase the quantity and quality of bone apposition.

The phenomena is seen at the attachment site of muscular fibers and on the tension side of teeth in orthodontic movement.

Electric stimulation has been used non-invasively with great success in healing chronic non-union fractures.

In tooth implants, I have discovered that I can enhance the load bearing capacity of the implant and supporting bone by the masticatory forces exerted on them by using a combined endosteal subperiosteal implant.

I can accomplish the same result in other types of bone implants.

The object of my invention is to provide an electric stimulating construction with a self-contained electric generating unit for stimulating osteoblastic activity.

These and other objects will become apparent as will be seen from a consideration of the following description and claims, and of the drawing, in which:

Figure 1:
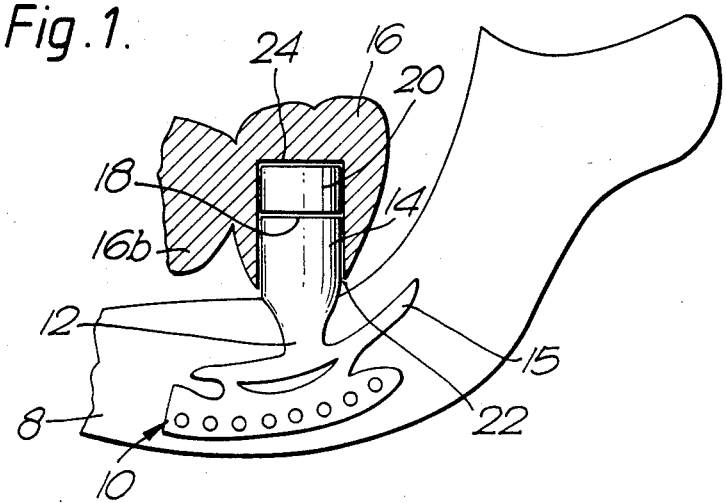
FIG. 1 is a cross-sectional view of the self-contained electric generator positioned as an example between the crown of a tooth and the implant.

More particularly in the implant 10, shown in FIG. 1., there is provided a seating flange 12 for distributing the stresses on the jaw bone 8 brought about by the masticatory forces.

Projecting from the flange 12 is the post 14 upon which the tooth crown 16 is connected.

Endosteal portion 15 is incorporated into the flange 12 for further positioning the flange on the jaw bone.

The post 14 may be cylindrical in shape with a flat top 18, upon which is preferably sealed a piezo electric element 20 in the form of a thin wafer.

The tooth crown 16 is provided with a recess 22, forming a close sliding fit over the end of the post 14 with a flat inner shoulder 24, for compressing the piezo electric wafer 20 when the jaws are compressed as in the masticatory process.

The compression of the jaws will cause the tooth crown 16 to intermittently compress the wafer at the shoulder 24 against the top surface 18 of the post 14, thus generating an intermittent electric current of the desired microamperage (about 0.2 to 2.0) flowing intothe jawbone to provide osteoblastic stimulation.

The electric stimulating construction can be incorporated into a movable bridge tooth 16 which is electrically connected at 16b to the anchor teeth, not shown where the stimulation may also take place to encourage bone apposition around a periodontally involved tooth.

The device may also be incorporated in the leg and arm structure and possibly the spine and neck where movement is normal. This is shown in FIG. 2. for example, in the knee implant, to encourage bone apposition at the implant-bone interface.

Figure 2:
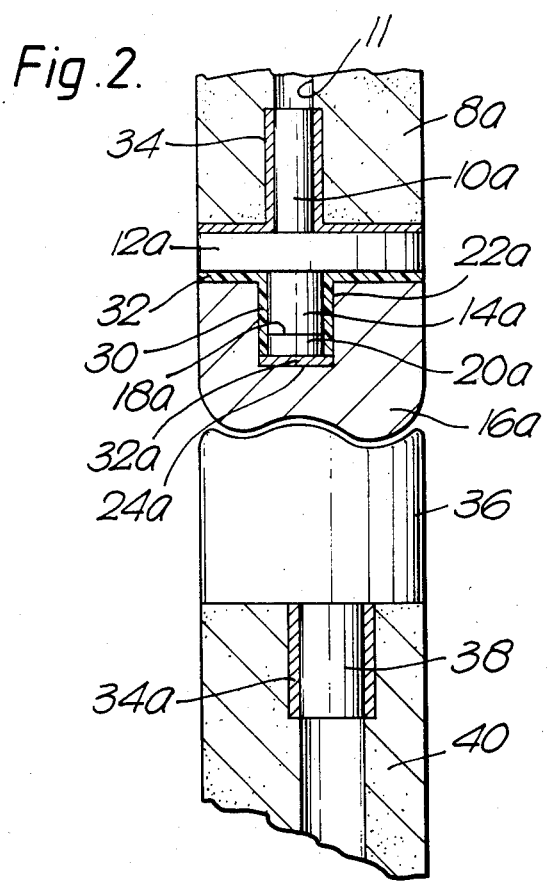
FIG. 2 is a similar view of the same invention incorporated in a front implant.

In FIG. 2, the corresponding parts of FIG. 1. in the implant construction are similarly numbered except for added "a".

Thus in bone 8a is seated the metal implant 10a having the post 14a with flat end 18a, which operates in the recess 22a to compress the piezo electric crystal 20a against the inner shoulder 24a to produce the desired osteoblastic stimulating currentflow.

The bottom of the cup should be a hardened conductive section to resist compression when pressure is applied to the piezo crystal.

The implant 10a, is shaped in cross-section to permit insertion into the marrow channel 11 of bone 8a.

It is may be desireable to facilitate the osteoblastic process, to cover the bone-contacting surface of the implant with a porous layer to permit osseous infiltration into the layer, thereby promoting growth constantly by the stimulating current.

This may be achieved by forming the contacting layer 34 by a flame spray, wire mesh, or sintered material which is sufficiently conducting to facilitate the osteoblastic stimulation by the current flow.

The opposite contacting part of the implant, can be the complementary cap 36 with its marrow chamber post 38 inserted into the bore 40. The cap 36 may be similarly covered with a porous layer 34a to provide osseous infiltration.

If it is desired to stimulate the osteoblastic process in the bone 40, the section 32a should be made of conductive material to allow the current to flow in cap 36.

In place of the piezo electric generating unit, other current mechanisms may be used which require a periodic pressure and release for producing the current flow. In such case it may be advantageous to make the flange 32 of silicone rubber.

I hereby claim;

1. An electric osteoblastic stimulating implant for direct electric contact with the skeletal structure which consists of a current carrying base section having an integrally formed bone connecting extension, for rigid connection into the skeletal structure; and a current carrying head section movably mounted to the base section; a cup shaped chamber formed in one of the sections and opening between the sections, an integrally formed post extending from the other section, and forming a close sliding fit into the chamber, a pressure-responsive electriccurrent producing unit contained in the chamber, said head section operating the current producing unit to cause current to flow into the skeletal structure.

2. The implant of claim 1, wherein the integrally formed bone connecting extension for rigid connection in the skeletal structure is provided with a porous surface to permit osseous infiltration into the porous surface, thereby promoting growth and a more rigid connection between the implant and the skeletal structure.

* * * * *